United States Patent [19]

Shank

[11] Patent Number: 5,753,694

[45] Date of Patent: May 19, 1998

[54] ANTICONVULSANT DERIVATIVES USEFUL IN TREATING AMYOTROPHIC LATERAL SCLEROSIS (ALS)

[75] Inventor: Richard P. Shank, Blue Bell, Pa.

[73] Assignee: Ortho Pharmaceutical Corporation, Raritan, N.J.

[21] Appl. No.: 881,023

[22] Filed: Jun. 23, 1997

Related U.S. Application Data

[60] Provisional application No. 60/022,006 Jun. 28, 1996.

[51] Int. Cl.[6] .................. A61K 31/35; A61K 31/18
[52] U.S. Cl. .................. 514/455; 514/454; 514/456; 514/459; 514/601
[58] Field of Search .................. 514/455, 454, 514/456, 459, 601

[56] References Cited

U.S. PATENT DOCUMENTS 5,384,327   1/1995   Constanzo et al. .................. 514/456

*Primary Examiner*—William R.A. Jarvis
*Attorney, Agent, or Firm*—Ralph R. Palo

[57] ABSTRACT

Disclosed herein is a method of treating amyotrophic lateral sclerosis with topiramate and related compounds.

4 Claims, No Drawings

ANTICONVULSANT DERIVATIVES USEFUL IN TREATING AMYOTROPHIC LATERAL SCLEROSIS (ALS)

This application claims priority to provisional application Ser. No. 60/022,006, filed Jun. 28, 1996.

BACKGROUND OF THE INVENTION

Compounds of Formula I:

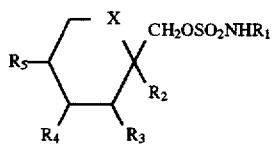

are structurally novel antiepileptic compounds that are highly effective anticonvulsants in animal tests (Maryanoff, B. E, Nortey, S. O., Gardocki, J. F., Shank, R. P. and Dodgson, S. P. *J. Med. Chem.* 30, 880–887,1987; Maryanoff, B. E., Costanzo, M. J., Shank, R. P., Schupsky, J. J., Ortegon, M. E., and Vaught J. L. Bioorganic & Medicinal Chemistry Letters 3, 2653–2656, 1993, McComsey, D. F. and Maryanoff, B. E., J. Org. Chem. 1995). These compounds are covered by U.S. Pat. No. 4,513,006. One of these compounds 2,3:4,5-bis-O-(1-methylethylidene)-β-D-fructopyranose sulfamate known as topiramate has been demonstrated in clinical trials of human epilepsy to be effective as adjunctive therapy or as monotherapy in treating simple and complex partial seizures and secondarily generalized seizures (E. FAUGHT, B. J. WILDER, R. E. RAMSEY, R. A. REIFE, L D. KRAMER, G. W. PLEDGER, R. M. KARIM et. al., Epilepsia 36 (S4) 33, 1995; S. K. SACHDEO, R. C. SACHDEO, R. A. REIFE, P. LIM and G. PLEDGER, Epilepsia 36 (S4) 33, 1995), and is currently marketed for the treatment of simple and complex partial seizure epilepsy with or without secondary generalized seizures in Great Britain, Finland, the United States and Sweden and applications for regulatory approval are presently pending in numerous countries throughout the world.

Compounds of Formula I were initially found to possess anticonvulsant activity in the traditional maximal electroshock seizure (MES) test in mice (SHANK, R. P., GARDOCKI, J. F., VAUGHT, J. L., DAVIS, C. B., SCHUPSKY, J. J., RAFFA, R. B., DODGSON, S. J., NORTEY, S. O., and MARYANOFF, B. E., Epilepsia 35 450–460, 1994). Subsequent studies revealed that Compounds of Formula I were also highly effective in the MES test in rats. More recently topiramate was found to effectively block seizures in several rodent models of epilepsy (J. NAKAMURA, S. TAMURA, T. KANDA, A. ISHII, K. ISHIHARA, T. SERIKAWA, J. YAMADA, and M. SASA, Eur. J. Pharmacol. 254 83–89,1994), and in an animal model of kindled epilepsy (A. WAUQUIER and S. ZHOU, Epilepsy Res. 24, 73–77, 1996).

Recent preclinical studies on topiramate have revealed previously unrecognized pharmacological properties which suggest that topiramate should be effective in treating some other neurological disorders. One of these is amyotrophic lateral sclerosis (ALS).

DISCLOSURE OF THE INVENTION

Accordingly, it has been found that compounds of the following formula I:

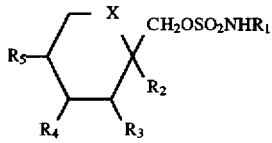

wherein X is O or $CH_2$, and $R_1$, $R_2$, $R_3$, $R_4$ and $R_5$ are as defined hereinafter are useful in treating acute amyotrophic lateral sclerosis (ALS).

DETAILED DESCRIPTION OF THE PREFERRED EMBODIMENTS

The sulfamates of the invention are of the following formula (I):

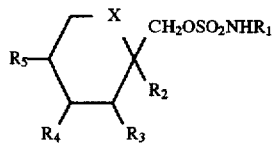

wherein

X is $CH_2$ or oxygen;

$R_1$ is hydrogen or alkyl; and $R_2$, $R_3$, $R_4$ and $R_5$ are independently hydrogen or lower alkoxyl, when X is oxygen, $R_2$ and $R_3$ and/or $R_4$ and $R_5$ together may be a methylenedioxy group of the following formula (II):

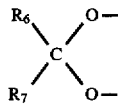

wherein $R_6$ and $R_7$ are the same or different and are hydrogen, lower alkyl or are alkyl and are joined to form a cyclopentyl or cyclohexyl ring.

$R_1$ in particular is hydrogen or alkyl of about 1 to 4 carbons, such as methyl, ethyl and iso-propyl. Alkyl throughout this specification includes straight and branched chain alkyl. Alkyl groups for $R_2$, $R_3$, $R_4$, $R_5$, $R_6$ and $R_7$ are of about 1 to 3 carbons and include methyl, ethyl, iso-propyl and n-propyl.

A particular group of compounds of formula (I) are those wherein X is oxygen and both $R_2$ and $R_3$, and $R_4$ and $R_5$ together are methylenedioxy groups of the formula (II), wherein $R_6$ and $R_7$ are both hydrogen, both alkyl, or combine to form a spiro cyclopentyl or cyclohexyl ring, in particular where $R_6$ and $R_7$ are both alkyl such as methyl. A second group of compounds are those wherein X is $CH_2$ and $R_4$ and $R_5$ are joined to form a benzene ring. A third group of compounds of formula (I) are those wherein both $R_2$ and $R_3$ are hydrogen.

The compounds of formula (I) may be synthesized by the following methods:

(a) Reaction of an alcohol of the formula $RCH_2OH$ with a chlorosulfamate of the formula $ClSO_2NH_2$ or $ClSO_2NHR_1$ in the presence of a base such as potassium a-butoxide or sodium hydride at a temperature of about −20° to 25° C. and in a solvent such as toluene, THF or dimethylformamide wherein R is a moiety of the following formula (III):

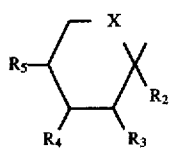

(b) Reaction of an alcohol of the formula RCH$_2$OH with sulfurylchloride of the formula SO$_2$Cl$_2$ in the presence of a base such as triethylamine or pyridine at a temperature of about −40° to 25° C. in a solvent such as diethyl ether or methylene chloride to produce a chlorosulfate of the formula RCH$_2$OSO$_2$Cl.

The chlorosulfate of the formula RCH$_2$OSO$_2$Cl may then be reacted with an amine of the formula R$_1$ NH$_2$ at a temperature of abut 40° to 25° C. in a solvent such as methylene chloride or acetonitrile to produce a compound of formula (I). The reaction conditions for (b) are also described by T. Tsuchiya et al. in Tet. Letters, No. 36, p. 3365 to 3368 (1978).

(c) Reaction of the chlorosulfate RCH$_2$OSO$_2$Cl with a metal azide such as sodium azide in a solvent such as methylene chloride or acetonitrile yields an azidosulfate of the formula RCH$_2$OSO$_2$N$_3$ as described by M. Hedayatullah in Tet. Lett. p. 2455–2458 (1975). The azidosulfate is then reduced to a compound of formula (I) wherein R$_1$ is hydrogen by catalytic hydrogenation, e.g. with a noble metal and H$_2$ or by heating with copper metal in a solvent such as methanol.

The starting materials of the formula RCH$_2$OH may be obtained commercially or as known in the art. For example, starting materials of the formula RCH$_2$OH wherein both R$_2$ and R$_3$, and R$_4$ and R$_5$ are identical and are of the formula (II) may be obtained by the method of R. F. Brady in Carbohydrate Research, Vol. 14, p. 35 to 40 (1970) or by reaction of the trimethylsilyl enol ether of a R$_6$COR$_7$ ketone or aldehyde with fructose at a temperature of about 25° C., in a solvent such a halocarbon, e.g. methylene chloride in the presence of a protic acid such as hydrochloric acid or a Lewis Acid such as zinc chloride. The trimethylsilyl enol ether reaction is described by G. L. Larson et al in J. Org. Chem. Vol. 38, No. 22, p. 3935 (1973).

Further, carboxylic acids and aldehydes of the formulae RCOOH and RCHO may be reduced to compounds of the formula RCH$_2$OH by standard reduction techniques, e.g. reaction with lithium aluminum hydride, sodium borohydride or borane-THF complex in an inert solvent such a diglyme, THF or toluene at a temperature of about 0° to 100° C., e.g. as described by H. O. House in "Modern Synthetic Reactions", 2nd Ed., pages 45 to 144 (1972).

The compounds of formula I: may also be made by the process disclosed U.S. Pat. No. 4,513,006, which is incorporated by reference herein.

The compounds of formula I include the various individual isomers as well as the racemates thereof, e.g., the various alpha and beta attachments, i.e., below and above the plane of the drawing, of R$_2$, R$_3$, R$_4$ and R$_5$ on the 6-membered ring. Preferably, the oxygens of the methylenedioxy group (II) are attached on the same side of the 6-membered ring.

The activity of the compounds of formula I in treating amyotrophic lateral sclerosis (ALS) arises from studies which indicate that topiramate exerts an antagonistic effect on the AMPA/kainate subtype of glutamate receptors (The R. W. Johnson Pharmaceutical Research Institute, Internal Research Report, Document ID Accession No. A500,960; J. W. GIBBS III, S. SOMBATI, R. J. DELORENZO, and D. A. COULTER, Epilepsia 37, in press, 1996), and that ALS is a chronic neurodegenerative disorder in which the regulation of glutamate is impaired (J. D. ROTHSTEIN, M. VAN KAMMEN, A. I. LEVEY, L. J. MARTIN and R. W. KUNCI, Annals Neurology 38, 73–84). Glutamate is utilized as the major excitatory neurotransmitter in the CNS. This function is served by a physiological process in which glutamate molecules are stored in vesicles within synaptic terminals of neurons. These molecules are released into the synaptic cleft when an action potential depolarzes the synaptic membrane, whereupon they activate specific receptors in the postsynaptic membrane of target neurons. Subsequently, the molecules are removed from the synaptic cleft by protein "transporters" in the membrane of the synaptic terminal of the presynaptic neuron and the surrounding glial cells (astrocytes). In ALS the activity of these transport proteins apppears to be abnormally low, which can cause an abnormal increase in the concentration of glutamate within the synaptic cleft. This in turn can cause an excessive activation of glutamate receptors, which, if sufficient, can induce neuronal cell death (J. D. ROTHSTEIN, In: *Pathogenesis and Therapy of Amyotrophic Lateral Sclerosis*, Edited by G. Serratrice and T. Munsat, Advances in Neurology 68, 7–20, Lippincott-Raven Publishers, Philadelphia,1995).

Studies have revealed that topiramate antagonizes the neuronal excitatory activity kainate, an analog of glutamate that selectively activates some subtypes of glutamate receptors (J. W. GIBBS II, S. SOMBATI, R. J. DELORENZO, and D. A. COULTER, Epilepsia 37, in press, 1996; The R. W. Johnson Pharmaceutical Research Institute, Internal Research Reports, Document ID Accession Numbers A500, 960 and 398533:1). In these studies, primary cultures enriched in neurons derived from the hippocampus of fetal rats were grown in vitro for 14 to 21 days under conditions that allowed them to reach a high density and develop numerous synaptic contacts. Perforated whole-cell patch-clamp procedures were used to study electrical properties of the neuronal membranes. In this procedure electrical contact between the recording electrode and the intracellular fluid is achieved by using amphotericin B to form pores in the cell membrane. This enables the cell membrane potential or current flow across the cell membrane to be recorded accurately. Kainate, topiramate and other test compounds were microperfused onto the neurons using a multi-barrel Teflon concentration clamp pipette. Topiramate (dissolved in DMSO at 1M, then diluted in the medium in which the neurons were incubated) was applied at concentrations of 0.01, 0.1, 1, 10 or 100 and kainate was applied at concentrations 0.1 or 1 mM.

In an initial set of experiments, the antagonistic action of topiramate on kainate-evoked currents was determined as a function of the membrane potential. In experiments in which the kainate-induced membrane currents were recorded at voltage-clamped potentials ranging from −60 mV to +60 mV at 20 mV increments the magnitude of topiramate's antagonistic effect was found to decrease as the membrane was depolarized. Hence, topiramate was most effective at membrane potentials near the resting state.

The time-course of topiramate's antagonistic activity was evaluated in a second set of experiments. Kainate was pulsed into the bathing fluid for 3 sec at 1 min intervals, and once a baseline for the kainate-evoked current was established topiramate was applied constantly for a period ranging from a few min to 20 min. A partial block of the kainate-evoked current was evident within one min after topiramate was applied, but even at saturating concentrations the kainate-evoked current was reduced by only 20 to 40%. This effect was readily reversed if topiramate was withdrawn (washed out) within 5 min. However, if topiramate was applied constantly for more than 10 min, the magnitude of the antagonistic effect on the kainate-induced cell membrane currents increased markedly, and when topiramate was withdrawn the kainate-evoked current remained depressed. Concentration-response curves were generated for both phases of topiramate's blocking effect. The $EC_{50}$ was approximately 1 micromolar for each phase. However, the concentration required for a maximum response was approximately 0.1 mM for the first phase (phase I block) but only approximately 0.010 mM for second (phase II block).

Because of the compelling evidence that the functional state of glutamate receptors is regulated partly by protein kinases and phosphatases (L. Y. WANG, F. A. TAVERNA, X. P. HUANG, J. F. MACDONALD, and D. R. HAMPSON, Science 259, 1173–1175, 1993), the phase II blocking effect could be explained by dephosphorylation of the kainate-activated receptors. Based on evidence that cAMP-dependent protein kinase (PKA) modulates kainate activated receptors(L. Y. WANG, F. A. TAVERNA, X. P. HUANG, J. F. MACDONALD, and D. R. HAMPSON, Science 259, 1173–1175, 1993), a set of experiments was undertaken to determine if dibutyryl cyclic AMP could restore the excitatory activity of kainate subsequent to topiramate's phase II block; i.e., cause the "irreversible" effect to be reversed. These experiments revealed that dibutyryl cyclic AMP partially or totally restored the kainate-evoked current. In another set of experiments the nonspecific phosphatase inhibitor okadaic acid was applied at 1 micromolar prior to, and during, the application of topiramate to determine if inhibiting the dephosphorylation of the kainate activated receptors would prevent the phase II blocking effect of topiramate. Okadaic acid had little effect on kainate-evoked current prior to the application of topiramate, and did not affect the initial antagonistic effect of topiramate (phase I block); however, as expected the phase II block was prevented. These results indicate that topiramate directly or indirectly inhibits the ability of a protein kinase (PKA) to phosphorylate kainate-activatable receptors, which over time shifts the receptors into a dephosphorylated state in which they are desensitized (can not be activated).

Regardless of the mechanism by which topiramate antagonizes the action of kainate on glutamate receptors, this antagonistic effect would reduce the rate of receptor activation. In pathological situations in which there is excessive activation of glutamate receptors, as occurs in ALS, a drug-induced reduction in the activation of glutamate receptors will reduce neuronal cell death.

For treating amyotrophic lateral sclerosis (ALS), a compound of formula (I) may be employed at a daily dosage in the range of about 100 to 800 mg, usually two divided doses, for an average adult human. A unit dose would contain about 25 to 200 mg of the active ingredient.

To prepare the pharmaceutical compositions of this invention, one or more sulfamate compounds of formula (I) are intimately admixed with a pharmaceutical carrier according to conventional pharmaceutical compounding techniques, which carrier may take a wide variety of forms depending on the form of preparation desired for administration, e.g., oral, by suppository, or parenteral. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. Suppositories may be prepared, in which case cocoa butter could be used as the carrier. For parenterals, the carrier will usually comprise sterile water, though other ingredients, for example, for purposes such as aiding solubility or for preservation, may be included. Injectable suspensions may also be prepared in which case appropriate liquid carriers, suspending agents and the like may be employed. Topiramate is currently available for oral administration in round tablets containing 25 mg, 100 mg or 200 mg of active agent. The tablets contain the following inactive ingredients: lactose hydrous, pregelatinized starch, microcrystalline cellulose, sodium starch glycolate, magnesium stearate, purified water, carnauba wax, hydroxypropyl methylcellulose, titanium dioxide, polyethylene glycol, synthetic iron oxide, and polysorbate 80.

The pharmaceutical compositions herein will contain, per dosage unit, e.g., tablet, capsule, powder injection, teaspoonful, suppository and the like from about 50 to about 200 mg of the active ingredient.

What is claimed is:

1. A method for treating amyotrophic lateral sclerosis (ALS) comprising administering to a mammal afflicted with such condition a therapeutically effective amount for treating such condition of a compound of the formula I:

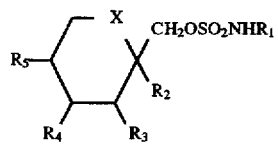

wherein

X is $CH_2$ or oxygen;

$R_1$ is hydrogen or alkyl; and $R_2$, $R_3$, $R_4$ and $R_5$ are independently hydrogen or lower alkyl and, when X is $CH_2$, $R_4$ and $R_5$ may be alkene groups joined to form a benzene ring and, when X is oxygen, $R_2$ and $R_3$ and/or $R_4$ and $R_5$ together may be a methylenedioxy group of the following formula (II):

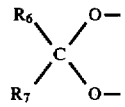

wherein $R_6$ and $R_7$ are the same or different and are hydrogen, lower alkyl or are alkyl and are joined to form a cyclopentyl or cyclohexyl ring.

2. The method of claim 1 wherein the compound of formula I is topiramate.

3. The method of claim 1, wherein the therapeutically effective amount is of from about 100 to 800 mg.

4. The method of claim 1, wherein the amount is of from about 25 to 200 mg.

* * * * *